United States Patent [19]

Harwell

[11] 4,365,092

[45] Dec. 21, 1982

[54] PROCESS FOR THE PREPARATION OF METHACRYLAMIDE FROM METHYLMETHACRYLATE

[75] Inventor: Kenneth E. Harwell, Merriam, Kans.

[73] Assignee: Cook Paint and Varnish Company, Kansas City, Mo.

[21] Appl. No.: 924,900

[22] Filed: Jul. 13, 1978

[51] Int. Cl.$^3$ ............................................ C07C 102/06
[52] U.S. Cl. .................................................. 564/135
[58] Field of Search ..................... 260/561 N; 564/135

[56] References Cited

U.S. PATENT DOCUMENTS

| | | | |
|---|---|---|---|
| 2,120,933 | 6/1938 | Dittmar | 260/561 N X |
| 3,397,232 | 8/1968 | Takagi et al. | 260/561 N |
| 3,666,809 | 5/1972 | Okeino et al. | 260/561 N |
| 3,887,425 | 6/1975 | Munch | 260/561 N X |
| 3,902,855 | 9/1975 | Lynch | 260/561 N X |
| 3,917,693 | 11/1975 | Asano et al. | 260/561 N |
| 3,929,421 | 12/1975 | Werges | 260/561 N X |

OTHER PUBLICATIONS

Arcus, J. Chem. Soc. 1949, pp. 2732–2736.
Organic Synthesis (vol. 4) John Wiley & Sons, N.Y.; N.Y. 1963, pp. 486–488.
Handbook of Chemistry & Physics, 49th Ed. 1968, The Chemical Rubber Co., pp. C-510 and F-85.

*Primary Examiner*—Arthur P. Demers
*Attorney, Agent, or Firm*—Cushman, Darby & Cushman

[57] ABSTRACT

This invention relates to an improved process for the preparation of methacrylamide by the reaction of methylmethacrylate with a molar excess of aqueous ammonium hydroxide at or near ambient temperatures to provide a high purity and yield of methacrylamide reaction product that is compatible in the preparation of isocyanate resins. Optional surfactants and alkoxide catalysts may be utilized to increase the rate of the reaction of methylmethacrylate with ammonia which may be further fostered by the addition of gaseous ammonia to the aqueous ammonium hydroxidemethylmethacrylate reaction mixture to yield methacrylamide according to the general equation:

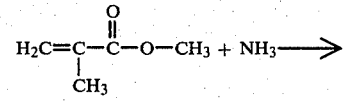

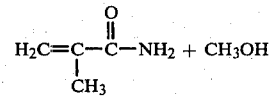

2 Claims, No Drawings

PROCESS FOR THE PREPARATION OF METHACRYLAMIDE FROM METHYLMETHACRYLATE

BACKGROUND OF THE INVENTION

1. Field of the Invention

This invention relates to the preparation of methacrylamide by reacting methylmethacrylate with a large molar excess of aqueous ammonium hydroxide in the temperature range of about 10° C. to about 40° C. More particularly, the process of the present invention provides a high yield high product quality methacrylamide which is readily isolated from the other reaction products and compatible in the preparation of isocyanate resins.

2. Description of the Prior Art

Methacrylamide is utilized in the preparation of isocyanate resins used in the formulation of paints and other coating compositions. The methacrylamide heretofore employed in such resinous compositions has generally been purchased from foreign sources that produce the methacrylamide by utilizing a high temperature process. Methacrylamide produced by this process is of acceptable purity in isocyanate resins but the cost of producing methacrylamide by these high temperature processes accounts for the high cost of this compound. Methacrylamide products have also been produced by other processes involving catalysts and variations of temperatures and processes using various feed stocks. However, the prior art processes heretofore available have generally required expensive equipment, elaborate separation equipment and techniques to separate the methacrylamide produced from the other by-products.

Another type of process such as the one disclosed in U.S. Pat. No. 2,451,436 prepares methacrylamide by reacting an amine with methylmethacrylate. The reaction conditions employed are rather harsh and as a result of elevated temperatures various by-products are produced which either require expensive separation techniques or result in a reaction product that is not compatible with the preparation of isocyanate resins.

The use of methacrylamide in isocyanate resin and resinous containing compositions such as paints and coating compositions has created a demand for high purity methacrylamide that can be produced in high yields at commercially attractive prices. The process for the production of methacrylamide should additionally employ inexpensive feedstocks and be an uncomplicated process providing a high yield high purity methacrylamide in which any by-products produced by the process should be fully compatible with the use of methacrylamide with isocyanate resinous compositions. Furthermore, a commercially attractive process should further allow the easy isolation of methacrylamide from any by-products produced in addition to a high selectivity for the production of the methacrylamide with corresponding high production yields.

SUMMARY OF THE INVENTION

The process of the present invention provides an inexpensive method for producing a high purity and high yield of methacrylamide at attractive commercial prices. The present process further provides a methacrylamide reaction product compatible in the preparation of isocyanate resins that is readily isolated from other reaction products. The present invention is economical and does not require expensive equipment for the conversion of methylmethacrylate into methacrylamide in accordance with the following reaction:

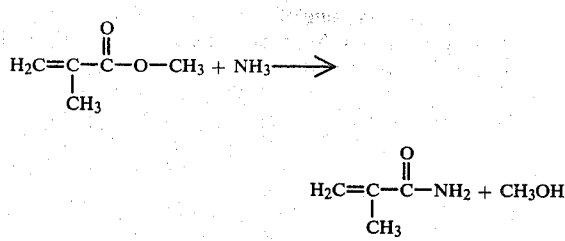

This reaction is performed by stirring methylmethacrylate with a large molar excess of aqueous ammonium hydroxide at or near temperatures in the range of about 10° C. to 50° C. The reaction achieves its optimal yields and advantages of isocyanate resin compatibility when the reaction temperature range is maintained from about 20° C.–25° C. with reaction rate being further affected by the ratio of water phase to the oil phase, and with the optional use of surfactants, catalysts and product work up during the course of the reaction.

The addition of methylmethacrylate to aqueous ammonium hydroxide at a temperature range of about 10° C. to about 50° C. will result in the formation of a methylmethacrylate oil phase and aqueous ammonium hydroxide phase. The methylmethacrylate oil phase is continuously stirred with the ammonium hydroxide aqueous phase for a period of up to about 40 hours. Optionally and in the preferred embodiment the reaction is enhanced by the continuous addition of ammonia gas to replace ammonia used in the reaction to reduce the reaction time. As the reaction proceeds, the oil phase slowly disappears, significantly the progress of and completion of the reaction of the methylmethacrylate with ammonia since the methacrylamide product is highly water soluble and may be recovered during or after the completion of the reaction. It will be recognized that the reaction of the present invention includes several parameters which effect the rate and the reaction products recovered in the process of the invention. These reaction parameters are temperature, ratio of water phase to oil phase, use of surfactants, catalysts and product workup. Each of these reaction parameters affect the rate of reaction and the reaction products attained and the compatability of the methacrylamide product and any resultant by-products with isocyanate resins utilized in paints and coating compositions. The main objective in the process of the invention for the production of high purity resin compatible methacrylamide is to reduce the reaction time by increasing the reaction rate without sacrificing the quality of the methacrylamide reaction product.

Reactions of methylmethacrylate with ammonium hydroxide at a temperature at or below 10° C. will slow the reaction to an almost imperceptible rate to yield a high quality product. Reactions at or above 55° C. will be complete in about 4 hours but will yield a predominantly polymerized product that is useless for present purposes. It has also been found that surfactants utilized as wetting agents and catalysts assist in the reaction mechanism. In addition product workup or the addition of ammonia gas under vacuum and the removal of methanol also assists in the reaction mechanism.

Upon completion of the reaction, the resulting solution is a mixture of ammonia, methanol, water, and methacrylamide. The resulting methacrylamide mixture may be recovered in any one of several ways cognizable to those skilled in the art. Such procedures may include vacuum distillation, filtration, and crystallization. The process in accordance with the present invention produces high yields approaching a 100 percent conversion of methylmethacrylate to methacrylamide which is directly compatible with the production of isocyanate resins.

DETAILED DESCRIPTION OF THE INVENTION

The advantages of the present invention are achieved by the reaction of methylmethacrylate with a molar excess of aqueous ammonium hydroxide in accordance with the following general equation:

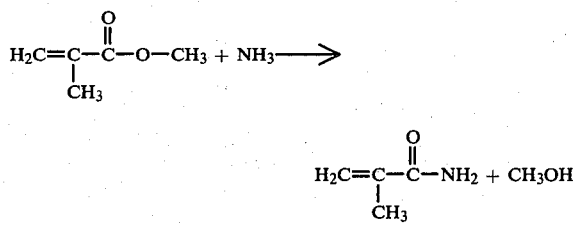

The reaction of methylmethacrylate with the molar excess of ammonium hydroxide is carried out by stirring methylmethacrylate with aqueous ammonium hydroxide in a temperature range of about 10° C. to about 50° C. The methylmethacrylate is initially present as an oil phase that forms a fairly stable two phase oil water system with the aqueous ammonium hydroxide phase. As the reaction proceeds, the oil phase slowly disappears to produce a single phase system, since the methacrylamide reaction product is a highly water soluble. The completion of the reaction is consequently visually determined by the disappearance of the insoluble methylmethacrylate oil phase. The reaction time generally spans a period of up to 40 hours depending on reaction conditions which are modified within limits to prevent the polymerization of the methylmethacrylate and the formation of unwanted by-products.

The benefits of the invention are optimally utilized when the reaction parameters or conditions are kept within certain ranges to allow the methylmethacrylate reaction to favor the formation of methacrylamide at the expense of an undesirable polymerization reaction. The conditions which favor the formation of the methacrylamide at the expense of the homo polymer are a function of (a) temperature; (b) ratio of water phase to oil phase; (c) surfactants; (d) catalysts; and (e) product workup. The foregoing reaction parameters or conditions may affect not only the rate of the reaction but also the mixture of by-products and the potential for the reaction to result in the formation of polymerized polymethyl methacrylate.

As a result, the main objective to be accomplished is reducing the reaction time while at the same time not sacrificing purity or utility of the methacrylamide product in isocyanate resin coatings.

One such parameter found to favor the formation of the methacrylamide is the periodic or continuous addition of ammonia gas to the system to replace ammonia used during the reaction. The preferred embodiment of the process of the present invention includes the continuous addition of ammonia gas for the duration of the reaction. This preferred procedure may be utilized along with other workup solution techniques including the removal of methanol and other reaction by-products along with the replenishing of ammonium hydroxide and methylmethacrylate while also removing the methacrylamide reaction product.

The temperature of the reaction effects not only the reaction rate but also the purity of the reaction product and the composition of other by-products. As heretofore discussed, if the temperature is below 10° C. the reaction rate will be almost imperceptible while a reaction at 55° C. will be complete in about four hours yielding a polymerized product. In achieving the advantages of the invention it has been found that temperatures in the range of about 10° C. and 50° C. may be utilized with the preferred range being about 20° C. to 25° C. to produce a high yield commercially usable methacrylamide product.

Related to the effect of temperature and reaction efficiency is the ratio of aqueous phase to oil phase in the reaction system. The greater the ratio of water phase to oil phase the shorter the reaction time. On the other hand, excess water in the system consumes greater energy in cooling the system and recovering the methacrylamide reaction product. In addition, if the resulting reaction solution is used directly in the making of a resin product, the water must be refluxed off or otherwise removed during which processing a homo polymer may form. In practice it has been found that a ratio of about three parts water by volume to one part methylmethacrylate by volume provides optimal reaction conditions when catalysts and surfactants are not utilized. In applications where a surfactant is utilized the rate of the reaction was not increased as significantly by the ratio of the respective solution volumes.

Surfactants which may be utilized to increase the reaction rate of the invention are in the nature of wetting agents which tend to make rather stable emulsions. Utilizing a three part by volume ammonium hydroxide aqueous solution to a one part per volume methylmethacrylate monomer and using a surfactant such as Polywet KX4 can reduce the reaction time from 18 hours to 13 hours when the amount of surfactant equals one percent of the total mixture. When two percent of Polywet KX4 is added to a 3,000 gram batch solution having a two parts by volume aqueous ammonium hydroxide to one part by volume of methylmethacrylate ratio, the reaction time was reduced from 40 hours to 17 hours. The fact that the surfactants form emulsions made the study of the reaction rates more difficult and also made the determination of the completion of the reaction more difficult since the final reaction solution was cloudy. In such cases a centrifuge may be employed to separate the layers and assist in the determination of the completion of the reaction.

Another method of increasing rate of the reaction is the utilization of catalysts. One such catalyst that may be employed to increase the reaction rate is sodium ethoxide. It is recognized in the prior art that catalysts such as sodium ethoxide or other catalysts having an alkoxide ion increase the nucleophilicity of the ammonia molecule due to the strong basicity of the alkoxide ion. When sodium ethoxide is added in an amount of about one percent of the total reaction mixture, the time for the completion of the reaction is about ten hours. As a further possible catalyst, "end of the reaction" conditions were simulated by adding methacrylamide and methanol to the reaction mixture at the start of the reaction. This procedure seemed to have little or no effect on reaction time.

In a further embodiment of the invention, product workup techniques were utilized as a mechanism for increasing the reaction rate and efficiency of the reaction. One such procedure employed which yields an exceptionally good product is achieved by placing the reaction mixture under a vacuum, and removing excess ammonia and methanol during the reaction which causes the reaction solution to cool and methacrylamide to precipitate out. The methacrylamide reaction product then may be filtered and removed as the reaction progresses. The removal of the methacrylamide precipitate during the course of the reaction may be repeated a number of times and if such methods are used, about 80 percent of the methacrylamide products may be recovered. As will be recognized by those skilled in the art, if a more concentrated solution is used, or a small volume ratio of aqueous ammonia hydroxide to the methylmethacrylate oil is utilized the reaction mechanism will favor the formation of the methacrylamide and consequently a greater portion of reaction product may be recovered by precipitation.

Upon completion of the reaction the two layers become a single solution of methacrylamide product which may be recovered by a variety of known recovery techniques. One such technique includes the recovery of the crystallized methacrylamide product from the cool reaction solution as hereinbefore discussed. In addition, the methacrylamide may be recovered in a useful form for use in isocyanate resins by utilizing the mixture of reaction products as herebefore described by removing excess ammonia, methanol and water by vacuum distillation. In this recovery technique, vacuum is required to keep the distillation temperature low, preferably in the range of about 25° C. to 40° C. As the solution becomes more concentrated, solid crystalline methacrylamide is precipitated out, which then may be filtered out, dried and stored. Temperatures above 40° C. are to be avoided since considerable polymerization begins to occur.

A further method for the separation and utilization of the methacrylamide product from the reaction solution is to employ vacuum distillation which then is stopped just prior to the precipitation of methacrylamide. This solution then may be used directly in the polymerization of isocyanate resins.

A further method of separation may be accomplished by cooling the reaction mixture from room temperature to about minus 25° C. which causes the majority of the methacrylamide reaction product to precipitate. The precipitate may be then filtered, cooled and dried, resulting in a high purity product. The process of the present invention appears to give almost a 100 percent conversion of methylmethacrylate to methacrylamide. The product is generally a high yield, high purity methacrylamide which is compatible with and may be used directly for the polymerization of isocyanate resins.

The following examples are for the purpose of further illustrating the preparation of the methacrylamide reaction product by the process of the invention in which examples all percentages, unless otherwise specified, are percentages by weight.

EXAMPLE 1

Methylmethacrylate, 95 ml. (0.92 mols) was placed in a 500 ml erlenmeyer flask with 260 ml of concentrated aqueous ammonia (4.3 mols). The mixture was stirred at room temperature with a magnetic stirrer for six hours, at which time more than half of the methylmethacrylate (MMA) dissolved. The solution was then saturated with ammonia gas and allowed to sit over a weekend.

Over the weekend all the methylmethacrylate (MMA) had dissolved yielding a clear aqueous solution. This solution was distilled under house vacuum until it reached 34° C. at which time a slurry of solids had formed. The crystal reaction product was transferred to an open dish and dried under an air jet. The product was recrystallized from hot benzene and formed large, flake-like crystals. Infrared spectrum of the crystals showed them to be identical to high purity methacrylamide monomer obtained from foreign commercial sources utilizing high pressure techniques.

Not all of the reaction product dissolved in benzene. The insoluble material was extracted three times with hot benzene and dried. It was identified by solubility and infrared spectra as polymethacrylamide. The yield of polymer was about 8%.

EXAMPLE 2

To a 5 liter, 3-neck flask equipped for stirring, gas addition, and cooling was added 1001 g of methylmethacrylate (10 mols) and 2500 ml of ammonium hydroxide (39 mols ammonia) and stirred for 16 hours at which time about one half of the methylmethacrylate (MMA) had dissolved. An inhibitor, 1 gram of N-phenyl-1-naphthylamine (NPNA) was added and ammonia gas addition started. A cold water bath was placed around the flask to avoid heating and the temperature maintained near 27° C. After seven more hours only about 50 ml of methylmethacrylate (MMA) remained unreacted, and after stirring overnight all of the methylmethacrylate (MMA) had dissolved. The mixture was stirred for a total time of 40 hours at 25°–27° C.

The reaction mixture was divided into two halves for workup by different methods. To one half was added 1 gram of N-phenyl-1-naphthylamine (NPNA) inhibitor and the solution was distilled under house vacuum. The temperature soon dropped to 10° C., and then gradually rose to 40° C., over a period of one-and-a-half hours. The mixture was quickly cooled to 25° C., and crystals of methacrylamide began to precipitate. Several hours later the crystals were filtered off and dried over a weekend, yielding 111 g. The dry material was extracted with warm methylethylketone (MEK) to separate any polymer and to recrystallize the methacrylamide. Seven grams of dry polymer was recovered. The recrystallized methacrylamide was in the form of large, clear crystals, weighing 25 g. The infrared spectrum of the crystals was identical to the foreign commercial sources of the methacrylamide monomer.

The filtrate from the first crystals contained an estimated 30% methacrylamide and weighed about 930 g. This solution was used directly in the polymerization of a copolymer resin, XA-3178-E4X7.

The second half of the reaction mixture was cooled to −25° C. in a dry-ice bath. Crystals began to form at +10° C. and at −25° C. a thick slurry was present. This was filtered in portions on a buchner funnel which had been previously cooled in a dry-ice chest. The collected crystals were dried on a sheet of filter paper over a weekend, dry weight 215 g. A titration for acid indicated the crystals contained about 3% methacrylic acid. Their infrared spectra was essentially identical to purchased methacrylamide.

The filtrate was evaporated under an IR heat lamp with a jet of air. It was partially polymerized due to heating, and its dry weight was near 200 grams. The theoretical yield of methacrylamide is 851 grams. Since over 400 grams were accounted for in each half of the reaction mixture the yield was very good. It appears that the conversion of methymethacrylate was near 100% and the yield of methacrylic acid was 3–6%.

The isocyanate copolymers were produced in accordance with procedures set forth in the allowed U.S. application Ser. No. 519,660 filed Oct. 31, 1974, which will issue to a common assignee, are being relied upon and incorporated herein by reference.

The properties of the different resins are listed below.

| CODE | XA-3178-E4X3 | XA-3178-E4X6 | XA-3178-E4X7 |
|---|---|---|---|
| MACA* SOURCE | P | C20C | C20B |
| MACA WT. % | 15 | 15 | 15 |
| BA** WT. % | 85 | 85 | 85 |
| SOLVENT | T-71*** | T-71*** | T-71*** |
| Wt./Gal. | 8.30 | 8.36 | 8.38 |
| COLOR | 1 | 3 | 3–4 |
| SOLIDS | 35.3% | 35.6% | 32.8% |
| ACID NO. | 2.5 | 5.1 | 25.9 |
| VISCOSITY | A- | A- | A- |

P - Indicates methacrylamide monomer from the Rohm & Haas Co in Germany.
C20C - Indicates methacrylamide we prepared and separated by low temperature crystallization.
C20B - Indicates methacrylamide remaining in the concentrated reaction liquor.
*MACA is methacrylamide
**BA is butylacrylate
***T-71 is Ethyleneglycol monoethylether acetate

EXAMPLE 3

To a five liter, 3-neck round bottomed flask equipped for stirring, ammonia gas addition and cooling with an ice water bath was added 1,001 grams (10 mols) of methylmethacrylate (MMA) and 2,200 grams of aqueous ammonia. No noticable heat was evolved upon the mixing of the aqueous ammonia with the methylmethacrylate. However, the ammonium salt of the inhibitor was formed and made the aqueous layer dark red. Temperature of the mixture was 10° C. and after 45 minutes, ammonia gas was bubbled through the stirred reaction mixture. A small balloon was used to keep a slight positive pressure. Temperature then rose over a ten-minute period to 21° C. at which point it was cooled down to 12° C. After six additional hours of reaction time, stirring was stopped to check the progress of the reaction. When the two layers had separated, little or no reaction was indicated at which point the cold bath was removed and the reaction mixture was stirred for eight more hours. The next morning, a white solid precipitate was present, indicating polymerization has occurred. The reaction mixture was filtered to remove the polymer. The remaining solution was cooled in a dry ice isopropyl alcohol bath to freeze out remaining methacrylamide (MACA). 300 grams of the crystalline product was recovered in this experiment. Theoretically yield is 800 grams and the actual yield of example is 35 percent.

EXAMPLE 4

One gram of N-phenyl-1-naphthylamine (NPNA) and 1,001 grams of methylmethacrylate (MMA) were added to a five liter, 3-neck flask equipped with a stirrer and gas addition inlet. Two thousand and fifty (2,050) grams of aqueous ammonium hydroxide was added, the stirrer started, and a balloon attached to provide a positive pressure. The temperature went from ambient temperature to 40 degrees in one hour. After four hours the temperature dropped to 35° C. The flask was cooled to 27° C. with cold water. The reaction mixture was then stirred for eight more hours. The next morning, the mixture had polymerized and was filtered to remove the polymer. The resulting solution was cooled in the bath and 180 grams of methacrylamide (MACA) were recovered to provide a 21 percent yield.

EXAMPLE 5

Three thousand (3,000) grams of aqueous ammonium hydroxide ($NH_4OH$) and two grams of N-phenyl-1-naphthylamine (NPNA) were placed in a five liter, 3-neck flask equipped with stirrer, ammonia inlet and cold water bath. One thousand and one (1,001) grams of methylmethacrylate (MMA) were added to the stirred mixture and ammonia gas addition started. After 18 hours of stirring and ammonia gas addition, the reaction was complete. Vacuum was applied to remove the excess ammonia gas and methanol. The temperature dropped to 0° C. and crystals formed. When the solution became rather thick, it was filtered and the vacuum again applied. This was done three times and the combined product weighed 640 grams to result in about a 75.3 percent yield.

The remaining solution was then cooled and concentrated, hydrochloric acid added until a PH of 7.4 attained. Sodium chloride was added to the solution until the solution was saturated. No result was observed and the solution was discarded.

EXAMPLE 6

A 5 liter, 3-neck flask equipped with stirrer and ammonia gas addition was charged with 1,000 grams of aqueous ammonium hydroxide ($NH_4OH$), 2 grams of N-phenyl-1-naphthylamine (NPNA) and 1,001 grams of methylmethacrylate (MMA). A cool water bath was then placed around the reaction flask and ammonia gas started. After 28 hours of reaction time the ammonia gas was shut off but stirring was continued for 12 more hours, at which time the reaction was complete. The product was then worked up in several ways.

Three hundred (300) grams of the reaction mixture was checked for PH and found to have a PH of 11.5. The solution was cooled in an ice bath and concentrated hydrochloric acid added to attain a PH of 7.3. Considerable heat was given off but the temperature was kept under 30° C. A solid precipitate formed and 300 grams of water was added to dissolve it. The solution was then saved for use in making a resin.

A second 300 gram portion of the reaction mixture was mixed with 300 grams of water and cooled in an ice bath. Concentrated hydrochloric acid was added to attain a PH of 7.2. The resulting solution was saved for use in making a resin.

Carbon dioxide gas was then bubbled through the remaining portion of the solution until a PH of 7.2 was attained. Fifteen hundred (1,500) grams of water were added to dissolve the solid precipitate which had formed. This solution was similarly saved and used for making a resin.

EXAMPLE 7

Two hundred (200) grams of aqueous ammonium hydroxide, two grams of N-phenyl-1-naphthylamine (NPNA) and 100 grams of methacrylamine (MACA) were added to a five liter, 3-neck flask with a cooling water bath surrounding it.

One thousand and one (1,001) grams of methylmethacrylate (MMA) was added to the stirred solution of ammonium hydroxide and ammonia gas addition started. The mixture was stirred for 14 hours and the next morning partial polymerization had taken place. The ammonia gas was started again and the mixture stirred for eight more hours. The solid polymer was filtered off and the remaining solution was cooled down and yielded 280 grams of methacrylamide (MCA) and 260 grams of polymer. The remaining solution was discarded.

EXAMPLE 8

One thousand and one (1,001) grams of methylmethacrylate was shaken with 300 grams of aqueous ammonium hydroxide in a two liter separatory funnel. The monomer was drawn off into a separate beaker and the aqueous layer containing a dark ammonium salt of the inhibitor was discarded. The procedure was repeated one more time and the monomer was added to 3,000 grams of aqueous ammonium hydroxide in a five liter, 3-neck flask with a cooling water bath around it. Ammonia gas was added and the reaction mixture was stirred for 18 hours to give a clear, colorless solution.

One thousand (1,000) grams of the reaction mixture was put into a separate beaker and carbon dioxide gas bubbled through the stirred solution in order to lower the PH. After six hours the PH had only been lowered from 11.4 to 9.1 and the solution was discarded. The remaining reaction was subjected to house vacuum for two hours. The PH was reduced from 11.4 to 10 and the solution was saved and employed in making resin.

EXAMPLE 9

One thousand and one (1,001) grams of methylmethacrylate (MMA) was washed with 500 grams of aqueous ammonium hydroxide (NH$_4$OH) and to that was added 3,000 grams aqueous ammonium hydroxide in a five liter, 3-neck flask equipped with a stirrer, gas inlet and water bath. To the stirred reaction mixture was added 40 grams of Polywet KX-4, a surfactant used to emulsify and disperse the reaction mixture. Ammonia gas was added for 13 hours until the reaction was complete. PH was measured at 11.6 and the mixture was used in making a resin.

EXAMPLE 10

Two portions of 250 grams aqueous ammonium hydroxide solutions were used to wash 1,001 grams of methylmethacrylate (MMA). The methylmethacrylate was added to 3,000 grams of aqueous ammonium hydroxide along with 200 grams of methacrylamide (MACA), and 64 grams of methanol in a five liter, 3-neck flask equipped with a stirrer and ammonia inlet. The mixture was stirred and a cool water bath placed around the flask. To the flask was added 40 grams of Aerosol 501, a surfactant which was stirred into the mixture while ammonia gas was bubbled through the reaction solution. After 13½ hours, the reaction was complete and the product was employed in making a resin.

EXAMPLE 11

One thousand and one (1,001) grams of methylmethacrylate (MMA) were washed with 500 grams of aqueous ammonium hydroxide (NH$_4$OH). The methylmethacrylate was then added to 2,000 grams of aqueous ammonium hydroxide in a five liter, 3-neck flask equipped with a stirrer and gas addition inlet. To the stirring reaction mixture was added 60 grams of Polywet KX-4 and a water bath was placed around the reaction flask. Ammonia gas was added for 17 hours, at which time the reaction had gone to completion. Due to the hazy appearance of the reaction solution, an aliquot of the reaction mixture was spun in a centrifuge for 20 minutes. A one phase solution was obtained. The resulting reaction solution containing methacrylamide was used for making a resin.

EXAMPLE 12

One thousand and one (1,001) grams of methylmethacrylate (MMA) was washed with 200 grams of aqueous ammonium hydroxide (NH$_4$OH). The methylmethacrylate was then washed with 300 grams of distilled water and the monomer was added to 300 grams of aqueous ammonium hydroxide in a five liter, 3-neck flask equipped with a stirrer and ammonia gas inlet. To the stirred mixture was added 40 grams of Polywet KX-4 and 40 grams of sodium ethoxide. After 10 hours of ammonia addition and stirring, the reaction was completed and the methacrylamide was recovered and used in making resin.

The invention has been discussed by way of example with reference to particular reaction conditions for producing the methacrylamide reaction product from methylmethacrylate. It will be recognized by those skilled in the art the present invention may be modified to produce methacrylamide by the reaction of methylmethacrylate with ammonium hydroxide by varying reaction rates and product yields, depending upon the reaction conditions and techniques employed. It will be further appreciated such that substitutions and modifications may be made in the process of the present invention by those skilled in the art without departing from the applicability or scope of the invention. These and various other modifications and substitutions may be made by those skilled in the art which are within the spirit and scope of the invention as defined in the following claims.

What is claimed is:

1. A process for the preparation of methacrylamide by the reaction of methylmethacrylate and ammonia comprising:

(a) adding methylmethacrylate and a surfactant to an aqueous solution of ammonium hydroxide wherein said ammonium hydroxide is used in amounts such that a molar excess of ammonium hydroxide is used per mol of methylmethacrylate to form a reaction mixture comprising a methylmethacrylate oil phase and an ammonium hydroxide aqueous phase;

(b) stirring said reaction mixture and maintaining the same at a temperature in the range of about 10° C. to 50° C. until said oil phase and said aqueous phase become a single phase and the reaction is completed; and (c) recovering methacrylamide from the resultant single phase reaction mixture comprising ammonia, water, methanol and methacrylamide, ammonia gas being continuously added to said reaction mixture as the reaction proceeds so as to resaturate the reaction mixture with ammonia gas while the reaction proceeds, the recovered methacrylamide being characterized by its compatibility for the preparation of isocyanate resins.

2. The process according to claim 1 wherein said surfactant is Polywet KX4.

* * * * *